United States Patent
Zaid et al.

(10) Patent No.: US 11,603,343 B2
(45) Date of Patent: Mar. 14, 2023

(54) INHIBITION OF DYRK1A KINASE

(71) Applicant: Ankh Life Sciences Limited, Dublin (IE)

(72) Inventors: Gene H. Zaid, Hutchinson, KS (US); Brian Scott Johnathan Blagg, Niles, MI (US); Cameron E. West, Hutchinson, KS (US)

(73) Assignee: Ankh Life Sciences Limited, Dublin (IE)

( * ) Notice: Subject to any disclaimer, the term of this patent is extended or adjusted under 35 U.S.C. 154(b) by 0 days.

(21) Appl. No.: 17/462,918

(22) Filed: Aug. 31, 2021

(65) Prior Publication Data

US 2022/0064091 A1     Mar. 3, 2022

Related U.S. Application Data

(60) Provisional application No. 63/073,541, filed on Sep. 2, 2020.

(51) Int. Cl.
*C07C 39/15* (2006.01)
*C07C 49/747* (2006.01)

(52) U.S. Cl.
CPC ............ *C07C 39/15* (2013.01); *C07C 49/747* (2013.01)

(58) Field of Classification Search
CPC ............................... C07C 39/15; C07C 49/747
See application file for complete search history.

(56) References Cited

U.S. PATENT DOCUMENTS

| | | | |
|---|---|---|---|
| 4,113,488 A | 9/1978 | Yamada et al. | |
| 4,939,196 A | 7/1990 | Sasaki et al. | |
| 5,663,032 A | 9/1997 | Fukui et al. | |
| 6,514,684 B2 * | 2/2003 | Suzuki | C07F 9/532 430/617 |
| 6,800,431 B2 * | 10/2004 | Miura | G03C 1/49827 430/619 |
| 7,314,693 B2 | 1/2008 | Ikegami et al. | |
| 7,534,539 B2 | 5/2009 | Obata et al. | |
| RE43,067 E | 1/2012 | Yoshitomo et al. | |
| 9,224,518 B2 | 12/2015 | Matsumura et al. | |
| 9,343,594 B2 | 5/2016 | Oya et al. | |
| 9,882,137 B2 | 1/2018 | Matsumuru et al. | |
| 9,929,348 B2 | 3/2018 | Matsushita et al. | |
| 10,875,859 B2 | 12/2020 | Zaid et al. | |
| 2007/0054207 A1 | 3/2007 | Kimura | |
| 2013/0165382 A1 | 6/2013 | Krantz et al. | |
| 2013/0225674 A1 | 8/2013 | Jose et al. | |
| 2016/0018932 A1 | 1/2016 | Nakayama et al. | |
| 2017/0252318 A1 | 9/2017 | Iwata et al. | |
| 2019/0062284 A1 | 2/2019 | Hulme et al. | |
| 2019/0315742 A1 | 10/2019 | Zaid et al. | |
| 2020/0101050 A1 | 4/2020 | Zaid et al. | |
| 2020/0102305 A1 | 4/2020 | Zaid et al. | |
| 2020/0102306 A1 | 4/2020 | Zaid et al. | |
| 2021/0276998 A1 | 9/2021 | Zaid et al. | |

FOREIGN PATENT DOCUMENTS

| | | |
|---|---|---|
| EP | 0440106 A2 | 1/1991 |
| EP | 0360014 B1 | 1/1996 |
| EP | 0328364 B1 | 5/1996 |
| EP | 0330504 B1 | 5/1996 |
| EP | 0332455 B1 | 6/1996 |
| EP | 2181853 B1 | 9/2015 |
| JP | 3791711 | 4/2006 |
| JP | 2017149658 | 8/2017 |
| WO | 2015084512 A1 | 6/2015 |
| WO | 2019178041 A1 | 9/2019 |
| WO | 2021178650 A1 | 9/2021 |

OTHER PUBLICATIONS

International Search Report and Written Opinion in PCT/US2021/048489, dated Mar. 28, 2022.
Liu et al. An ELISA DYRK1A non-radioactive assay suitable for the characterization of inhibitors, F1000Research, 2017, 6:42.
Stotani et al. "DYRK1A inhibition as potential treatment for Alzheimer's disease"; Future Med.Chem (2016).
Tian et al. "Nigegladines A-C, Three Thymoquinone Dimers from 'Nigella glandulifera'" Org. Lett. 2017, 19, 6348-6351 (doi: 10.1021/acs.orglett.7b03189).
Product Introduction: 2,2/'-Methylenebis(1,4-benzenediol). VulcanChem. Last Modified May 11, 2021.

* cited by examiner

*Primary Examiner* — Sikarl A Witherspoon
(74) *Attorney, Agent, or Firm* — Hovey Williams LLP

(57) ABSTRACT

Novel compounds which inhibit DYRK1A activity comprise thymoquinone derivatives including a pair of substituted or unsubstituted six-membered carbon rings selected from phenyl and cyclohexadiene linked by an alkyl or alkenyl linker. Each six-membered ring includes at least one oxygen-bearing substituent selected from carbonyl oxygens, hydroxyls, alkoxyls, and halogenated derivatives thereof. The compounds can be administered to mammalian subjects for inhibition of DYRK1A kinase proteins.

21 Claims, 1 Drawing Sheet

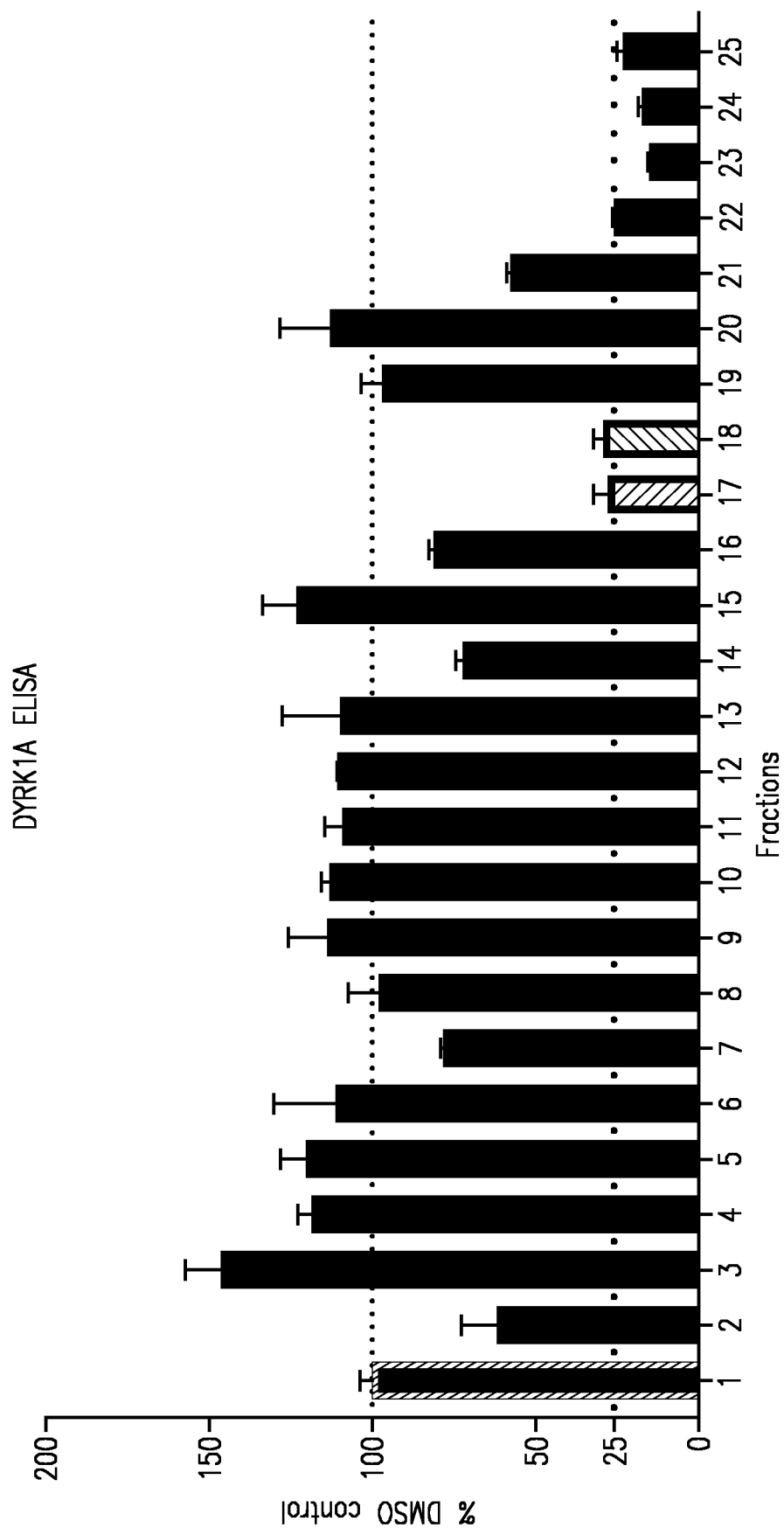

INHIBITION OF DYRK1A KINASE

CROSS-REFERENCE TO RELATED APPLICATIONS

The present application claims the priority benefit of U.S. Provisional Patent Application Ser. No. 63/073,541, filed Sep. 2, 2020, entitled INHIBITION OF DYRK1A KINASE, incorporated by reference in its entirety herein.

BACKGROUND OF THE INVENTION

Field of the Invention

The present invention is concerned with new thymoquinone derivative compounds and methods of use thereof. The compounds act as DYRK1A inhibitors when administered to a mammalian subject or when contacted with DYRK1A kinase.

Description of Related Art

As of 2016, an estimated 47,500,000 people worldwide were affected by dementia and this number is estimated to double by 2030 and triple by 2050, resulting in a huge burden on public health.

Alzheimer's disease (AD) is a neurodegenerative disease whose most common symptom is a progressive loss of cognitive functions and intellectual abilities, resulting in serious impairment of daily life activities. AD accounts for 70% of dementia cases globally and it is estimated that more than 20 million people are currently affected by it worldwide. In coming years, with the continuing aging of the global population, around 65 million individuals will likely be suffering from this pathology.

The causes of AD are still poorly understood. In addition to the genetic hypothesis, three hypotheses have been proposed to explain its insurgence:

According to the cholinergic hypothesis, AD is caused by a progressive decrease in the production of the neurotransmitter acetylcholine in the brain. Nowadays, this theory is accepted less than in the past, due to lack of robust clinical and pharmacological evidence.

According to the β-amyloid hypothesis, insoluble extracellular protein deposits called amyloid plaques (APs) are responsible for the neuronal death, synaptic degeneration, and adverse oxidative activity observed in the brains of AD patients. APs are mainly constituted by β-amyloid peptides (Aβ), generated by the cleavage of the amyloid precursor protein (APP) by β and γ-secretases, resulting in the formation of Aβ fragments, which are 37-42 amino acids in length ($A\beta_{37-42}$). These fragments can oligomerize to form soluble toxins that are supposed to initiate the adverse events previously mentioned. Furthermore, Aβ peptides can also aggregate to form the insoluble β-APs that are typically detected in AD brains.

According to the tau hypothesis, neuronal death is associated with the presence in AD brains of intracellular insoluble aggregates of hyperphosphorylated microtubule associated tau protein called neurofibrillary tangles (NFTs). Here, the aberrant activity of certain protein kinases is thought to lead to hyperphosphorylation of tau protein, thus initiating the subsequent aggregation of the protein into the neurotoxic NFTs.

Currently, pharmacological treatments of AD are limited to only two groups of drugs: acetylcholine esterase (ACE) inhibitors and memantine. While ACE inhibitors increase the neuronal levels of acetylcholine, memantine acts as an antagonist of the neuronal N-methyl-D-aspartate (NMDA) receptor, reducing the neuronal overstimulation caused by glutamic acid. Unfortunately, these drugs are not entirely effective and their benefits are limited to the early stages of the disease.

In the continuous quest for novel small molecules therapeutics as potential treatments for AD, medicinal chemists have recently turned their efforts toward the inhibition of several protein kinases involved in tau phosphorylation. For instance, targets such as GSK-3β, cdk5, p38, Erk1 and 2, JNK, CK1δ and CK1ε directly contribute to tau phosphorylation and several small molecule inhibitors of these proteins have been reported over the last two decades.

It is known that one of these kinases, DYRK1A (Dual Specificity Tyrosine Phosphorylation Regulated Kinase 1A), plays a part in the development of AD. The link between DYRK1A, aberrant AP formation, and tau pathology in AD brains has been studied, and small molecules have been proposed as selective inhibitors of DYRK1A.

DYRK1A is a eukaryotic serine-threonine protein kinase which belongs to the superfamily of the CMGC group of proline-arginine-directed serine-threonine kinases. The DYRK family is highly conserved and comprises five mammalian subtypes including 1A, 1B, 2, 3, and 4. Dual-specificity kinases phosphorylate a single tyrosine residue in their activation loop (Tyr321 in DYRK1A), thus catalyzing their auto-activation. This self-phosphorylative activity only relates to a transiently active protein intermediate state, which is then lost after translation. In addition to their auto-phosphorylative activity, DYRK proteins are known to phosphorylate several endogenous targets involved in a wide range of signaling pathways both in vitro and in vivo.

The DYRK1A gene is located in the Down syndrome critical region (DSCR) of chromosome 21 (21q22.2) and was identified as the candidate gene responsible for the effects of Down syndrome (DS), such as intellectual disability, microcephaly, and age-associated neurodegeneration. Structurally, the protein is divided into five main regions: at its N-terminal a bipartite nuclear localization signal (NLS), a kinase domain, a proline-glutamic acid-serine-threonine rich (PEST) domain, a consecutive histidine repeat (His), and a serine-threonine rich domain.

DYRK1A is expressed ubiquitously, and is abundant in the cerebellum, olfactory bulb, and hippocampus, and has been found to be upregulated during the early stages of development, followed by a gradual decrease to lower levels in later stages. During development, DYRK1A plays an important role in controlling brain growth through neuronal proliferation and neurogenesis. Different gene dosages of DYRK1A result in different phenotypes. DYRK1A null mutants did not survive midgestation. Mice heterozygous for the mutation exhibit decreased neonatal viability, reduced body size, and reduced number of neurons and neuron size in certain regions of the brain. Furthermore, the same animals displayed alteration of motor functions and impairment of special learning capacities. DYRK1A haploinsufficiency results in reduced brain size in mice.

Increased levels of DYRK1A have been reported in various areas of the brain of AD patients. In particular, the percentage of DYRK1A-positive nuclei in the frontal cortex of AD patients is approximately 10% compared with only 0.5% in normal brains. Similar levels of DYRK1A have been observed in brains affected by other neurodegenerative disorders, such as Parkinson's, Huntington's, and Pick's diseases. Unfortunately, the role of DYRK1A in these pathologies is not clear. However, expression of DYRK1A has been found to be increased 1.5-times in the brains of DS-affected people, when compared with the levels observed in people not affected by trisomy of chromosome 21.

DYRK1A is involved in two main neurodegenerative processes of AD: the formation of APs and NFTs. DYRK1A directly phosphorylates tau proteins at 11 serine and threonine residues, some of which have been detected to be phosphorylated in tau aggregates of NFTs of AD brains. Moreover, DYRK1A-mediated tau phosphorylation is capable to promote further tau phosphorylation by GSK-3β, thus resulting in additional accumulation of NFTs.

DYRK1A also phosphorylates the alternative splicing factor (ASF) at three different serine residues (Ser 227, Ser 234, and Ser 238), preventing its ability to regulate tau splicing and resulting in the formation of NFTs. DYRK1A can also phosphorylate regulator of calcineurin-1 (RCAN1) at Thr 192, slowing down its degradation and promoting its interaction with calcineurin (caln), thus inhibiting the phosphatase activity of caln on tau, and promoting accumulation of phosphorylated tau protein.

DYRK1A phosphorylation of presenilin 1 (PS1), a subunit of γ-secretase, enhances the proteolytic activity of γ-secretase itself, leading to increased production of neurotoxic Aβ peptides.

These observations would suggest a role of DYRK1A in the development of AD and inhibition of this target may be beneficial for AD patients, for example, by reducing syntomatology and improved life conditions. Accordingly, several groups have reported their efforts in the identification and optimization of DYRK1A inhibitors. However, to date, this research has not developed inhibitors which significantly ameliorate the symptoms of AD.

Therefore, there is a need in the art for new small molecule DYRK1A inhibitors which may provide effective treatment modalities.

SUMMARY OF THE INVENTION

The present invention provides new thymoquinone derivative compounds and tautomers which have demonstrated DYRK1A inhibition efficacy, as well as methods of inhibiting DYRK1A activities. Broadly speaking, the compounds of the invention are thymoquinone derivative compounds comprising a pair of substituted or unsubstituted six-membered carbon rings (e.g., a first and second ring) linked by a linker bonded to both of said six-membered rings, the linker being an alkyl or alkenyl group having from 1-6 carbon atoms. The first and second six-membered carbon rings are each selected from the group consisting of phenyl and cyclohexadiene. At least one of the six-membered rings has a pair of oxygen-bearing substituents selected from the group consisting of carbonyl oxygens (e.g. ketones), hydroxyl groups, alkoxyl groups, and halogenated derivatives thereof.

In one or more embodiments, the first and second six-membered rings are both phenyl and each of the respective oxygen-bearing substituents is a hydroxyl group, alkoxyl group, or halogenated derivative thereof. In one or more embodiments, one of the six-membered rings (e.g., the first ring) is phenyl and the other six-membered ring (e.g., the second ring) is cyclohexadiene, the oxygen-bearing substituents of the phenyl ring are a hydroxyl group, alkoxyl group, or halogenated derivative thereof, and the oxygen-bearing substituents of the cyclohexadiene ring are both carbonyl oxygens or halogenated derivatives thereof. In one or more embodiments, the respective oxygen-bearing substituents are in a para relationship to each other on each ring. Each of the first and second six-membered rings preferably includes at least one alkyl substituent having from 1-6 carbon atoms. In one or more embodiments, each of the first and second six-membered rings preferably includes an isopropyl group on each ring. In one or more embodiments, at least one six-membered ring in the pair includes a methyl substituent. In one or more embodiments, the linker is a $C_1$-$C_4$ alkyl group. In one or more embodiments, the linker is a $CH_2$ methylene bridge.

As used herein, the "compounds" of the invention respectively refer to the specifically defined compounds, as well as the isomers, tautomers, derivatives, solvates, degradation products, metabolites, esters, metal complexes (e.g., Cu, Fe, Zn, Pt, V), prodrugs, and pharmaceutically acceptable salts thereof, unless otherwise noted. As used herein, a derivative is a compound that can be imagined to arise or actually be synthesized from a parent compound by replacement of one atom with another atom or a group of atoms, provided the derivative retains at least the activity of the parent compound (e.g., the derivative may improve the activity, but not fundamentally alter the activity). In this case, the derivative compounds must nonetheless exhibit DYRK1A inhibition activity. Similarly, pharmaceutically acceptable salts with reference to the components of the composition means salts which are pharmaceutically acceptable, e.g., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, lauryl sulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenylsubstituted alkanoic acids, propionic acid, p-toluenesulfonic acid, pyruvic acid, salicylic acid, stearic acid, succinic acid, tartaric acid, tertiary butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Likewise, prodrugs are compounds designed so as to convert into the active compound, e.g., metabolize in vivo into the pharmacologically active compounds contemplated herein.

The methods of the invention include inhibition of DYRK1A activity by contacting DYRK1A kinase with an effective amount of a compound according to the embodiments described herein.

In one aspect, the methods comprise administering the compounds of the invention to a mammal in order to inhibit the activity of DYRK1A kinase in the mammal. The compounds may be administered in any convenient manner, such as by oral, rectal, nasal, ophthalmic, parenteral (including intraperitoneal, intravesical, gastrointestinal, intrathecal, intravenous, cutaneous (e.g., dermal patch), subcutaneous (e.g., injection or implant), or intramuscular) administrations. The dosage forms of the invention may be in the form of liquids, gels, suspensions, solutions, or solids (e.g., tablets, pills, or capsules). Dosage levels administered to mammalian subjects are quite variable owing to factors such as the subject's age, subject's physical condition, the type of condition(s) being treated, and the severity of the conditions. Determination of proper dosage levels can readily be determined by those skilled in the art. The mammalian subjects may include human subjects.

BRIEF DESCRIPTION OF THE DRAWING

FIG. 1 is a bar graph illustrating the inhibition of DYRK1A kinase using the preferred compounds of the invention, as compared with other similar compound mixtures.

DETAILED DESCRIPTION OF THE PREFERRED EMBODIMENTS

U.S. Pat. No. 10,875,859 (Dec. 29, 2020), U.S. Patent Publication 2020/0102305, filed Dec. 3, 2019, and co-pending U.S. Ser. No. 16/810,291, filed Mar. 5, 2020, each incorporated by reference herein in their entireties, describe new classes of compounds or adducts derived from the reaction between thymoquinone and various β-carbolines, particularly harmaline and related harmaline-like compounds. These compounds are disclosed as having anti-cancer activities, as well as being useful for the treatment of diabetes. These references do not teach or suggest that thymoquinone/β-carboline compounds or adducts have any utility as DYRK1A inhibitors, or as treatments for AD or other neurodegenerative diseases.

These references further describe processes for carrying out the reactions between thymoquinone and β-carbolines. These syntheses involve solubilizing respective quantities of thymoquinone and β-carbolines in a non-interfering solvent such as DMSO or a lower (C1-C4) alcohol, followed by an extended reaction period. Specifically, the reference teaches that the weight ratio of thymoquinone to harmaline should range from about 0.5:1 to 25:1, more preferably from about 0.7:1 to 6:1, and most preferably from about 1.5:1 to 3:1. In terms of weight amounts, the amount of thymoquinone should range from about 25-95% by weight, and the weight of amount of harmaline should be from about 5-75% by weight, with the total weight of these ingredients taken as 100% by weight. In most cases, however, it is preferred that the amount of thymoquinone be present in a weight excess relative to the amount of harmaline. The reaction duration should range from about 12 hours-4 weeks at a temperature ranging from about 20-60° C. In an alternative low-temperature synthesis method, thymoquinone and harmaline are mixed in a noninterfering solvent, and reacted at a temperature of less than about 10° C. Desirably, the reaction temperature is less than about 0° C., and more preferably ranges from about −10° C. to about 100° C. The reaction time is usually for a period of from about 4 hours to about 14 days, and more preferably from about 6-100 hours. Advantageously, the low-temperature conditions are maintained throughout the reaction period.

The reaction products described in these references generally comprise a β-carboline moiety and a thymoquinone moiety with an alkyl or alkenyl linker bonding the moieties. However, it has now been found that the reactions may also generate compounds made up of thymoquinone dimer derivatives with an alkyl or alkenyl linker bonding the moieties, and these thymoquinone derivatives have also been found to have significant activities as DYRK1A kinase inhibitors.

Generally speaking, certain new compounds of the invention have the following structures I and/or II:

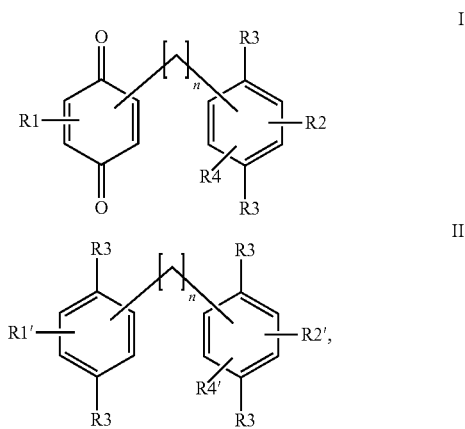

where the linker -[ ]$_n$- may be attached to the corresponding six-membered rings at any valence-permitted positions about the rings. In one or more embodiments, the linker -[ ]$_n$- is a straight or branched chain alkyl or alkenyl group, where n is from 1-6 (preferably 1-4, and preferably the linker is a methylene bridge). Each of R3 is independently selected from the group consisting of hydroxyls (OH), alkoxyls, straight and branched alkyl groups (preferably C1-C6 alkyls, more preferably C1-C4 alkyls), halogenated derivates thereof, and halogens, subject to the proviso that at least one of the six-membered rings in each pair comprises at least one oxygen-bearing substituent. In one or more embodiments, at least one ring comprises two oxygen-bearing substituents. In one or more embodiments, both rings comprise at least one oxygen-bearing substituent. In one or more embodiments, both rings each comprise two oxygen bearing substituents. Each of R1, R2, R4, R1', R2', and R4', inclusive, may be attached to the corresponding six-membered ring at any valence-permitted positions about the ring, and each of R1, R2, R4, R1', R2', and R4' are independently selected from the group consisting of —H, and straight and branched alkyl groups (preferably C1-C6 alkyls, more preferably C1-C4 alkyls). In one or more embodiments, one or more carbon atoms of the linker and/or any of R1, R2, R3, R4, R1', R2', or R4' may be independently substituted with a halogen (e.g., Cl, Br, or I) or hydroxyl group, with the proviso that at least one of R2 or R4 in compound I, or R2' and R4' in structure II is an isopropyl group. In one or more embodiments, at least one of R2 or R4 in compound I is a methyl group. In one or more embodiments, at least one R2' or R4' in compound II is a methyl group.

Further compounds in accordance with the invention may be selected from any one of the structures III-VI:
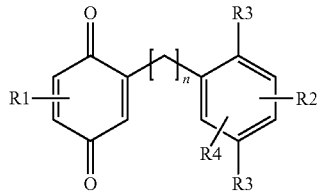
III
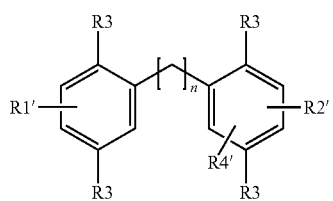
IV
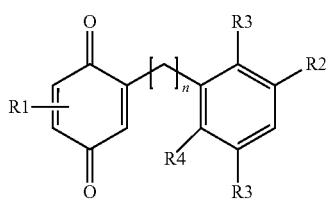
V
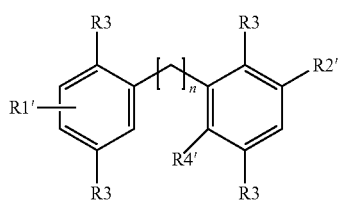
VI
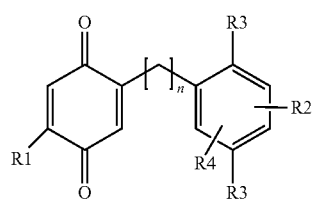
VII
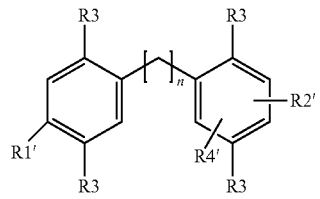
VIII
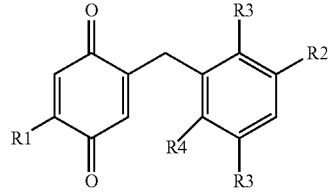
IX
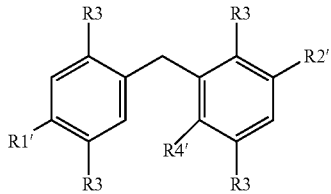
X
where n, R1-R4, and R1', R2', and R4' are all as defined above.
Particularly preferred compounds include:
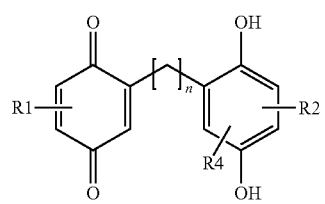
XI
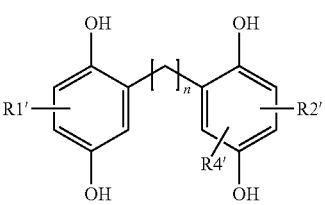
XII
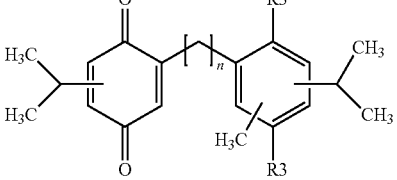
XIII
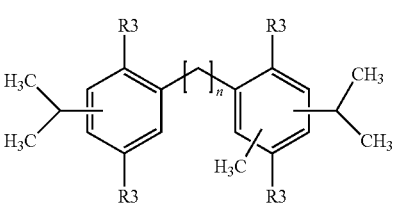
XIV
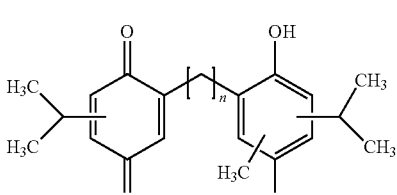
XV
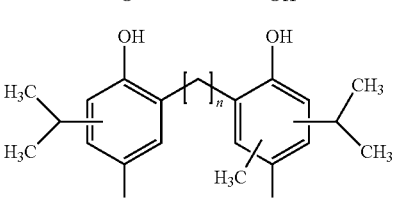
XVI
where the hydroxyl groups in any of the foregoing structures may be substituted with a halogen.

Particularly preferred compounds in accordance with the invention have the following structures XVII and/or XVIII:

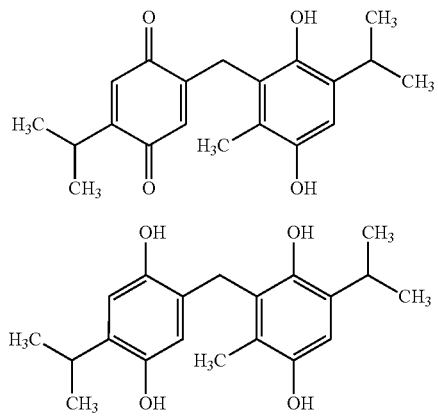

Pharmaceutically acceptable salts, derivatives, and/or prodrugs of any foregoing compounds can be used. Combinations of one or more of the foregoing compounds can also be used in the invention. In one or more embodiments, compounds according to embodiments of the invention are isomers, and in some cases tautomers of one another, wherein compositions of the invention will comprise a mixture of compounds having structure I and structure II, which will interconvert in solution.

Therapeutic compositions for inhibition of DYRK1A kinase are also contemplated herein. The compositions comprise a compound according to any of the embodiments described herein dispersed in a pharmaceutically-acceptable carrier. The term carrier is used herein to refer to diluents, excipients, vehicles, and the like, in which the compound(s) may be dispersed for administration. For example, the carrier may be any solution, suspension, powder, gel, etc., including isotonic solution, buffered and saline solutions, such as syrups or aqueous suspensions, etc. in which the compounds are dispersed. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would be selected to minimize any degradation of the compound or other agents and to minimize any adverse side effects in the subject. Pharmaceutically-acceptable ingredients include those acceptable for veterinary use as well as human pharmaceutical use, and will depend on the route of administration. For oral administration, the compounds can be formulated into conventional oral dosage forms such as solid preparations (for examples capsules, tablets), and liquid preparations (for example as syrups, elixirs and concentrated drops). Likewise, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like.

The composition can comprise a therapeutically effective amount of the compound(s) dispersed in the carrier. Combinations of compounds are also contemplated. Additional ingredients may be included with the compound(s) of the invention for administration to the subject. Such additional ingredients include, other active agents, preservatives, buffering agents, salts, flavoring agents, or other pharmaceutically acceptable ingredients.

The dosage forms of the invention may be in the form of liquids, gels, suspensions, solutions, or solids (e.g., tablets, pills, or capsules). The term "unit dosage form" refers to a physically discrete unit suitable as a unitary dosage for human or animal use. Each unit dosage form may contain a predetermined amount of the compound(s) optionally pre-dispersed in the carrier calculated to produce a desired effect.

The disclosed embodiments are suitable for various routes of administration, depending upon the particular carrier and other ingredients used. For example, the compound(s) or therapeutic compositions may be administered in any clinically suitable manner that produces contact of the active compound(s) with the desired site of action in the body of a subject, such as a human or animal, such as by oral, rectal, nasal, ophthalmic, parenteral (including intraperitoneal, intravesical, gastrointestinal, intrathecal, intravenous, cutaneous (e.g., dermal patch), subcutaneous (e.g., injection or implant), or intramuscular) administrations.

In use, a therapeutically effective amounts of the compound(s) or therapeutic compositions containing the compound(s) or prodrugs thereof, are administered to a mammalian subject in need thereof for a therapeutically effective amount of time. Thus, methods of inhibiting DYRK1A kinase activity in a subject are also disclosed. As used herein, a "therapeutically effective" amount refers to the dosage amount and/or duration that will elicit the biological or medical response of a tissue, system, or subject that is being sought by a researcher or clinician, and in particular elicit some desired therapeutic inhibition of detectable activity of DYRK1A. One of skill in the art recognizes that an amount or duration may be considered therapeutically "effective" even if the condition is not totally eradicated or prevented, but it or its symptoms and/or effects are improved or alleviated partially or inhibited from worsening in the subject. As used herein, "inhibitors" refer to compounds that partially or totally block stimulation, decrease, prevent, or delay activation, or inactivate, desensitize, or down-regulate activity of the target (DYRK1A) as compared to a control in a particular assay or in a patient. Similarly, the term "inhibition" means a partial or total blocking, stimulation, decrease, prevention or delaying of activation, or inactivation, desensitizing or down-regulation of activity of the target (DYRK1A) as compared to a control in a particular assay or in a patient. Inhibitory activity can be measured, for example, by the method described in the Example.

Such therapeutically effective dosages and durations may comprise a single unit dosage or, more usually, periodic (e.g., daily or weekly) administration of lower dosages over time. In some embodiments, upon administration, the prodrug mechanism of action entails enzyme-mediated, chemical, or spontaneous degradation or hydrolysis that converts the prodrug into an active metabolite (in some cases involving one or more intermediate compounds).

Dosages and dosage regimens under which the compound(s) are administered will vary according to the dosage form, mode of administration, the condition being treated, severity/stage of the condition, and particulars of the subject being treated (e.g., subject's age, physical condition).

Accordingly, optimal therapeutic concentrations will be best determined at the time and place through routine experimentation. For example, dosage of the compound(s) can be ascertained from any combination of factors: the pharmacodynamic characteristics of the particular compound(s) and its mode and route of administration; the age, health and weight of the recipient; the nature and extent of the symptoms; the kind of concurrent treatment; the frequency of treatment; and/or the effect desired. In one or more embodiments, the dosage of compound(s) to be administered can be determined by standard procedures taking into account standard benchmarks, such as a compound's $IC_{50}$, $EC_{50}$, and biological half-life in relation to the age, size and weight of the patient, and the disease or disorder associated with the patient. The importance of these and other factors to be considered are known to those of ordinary skill in the art. Amounts administered also depend on the routes of administration and the degree of oral bioavailability (should the compound(s) be administered via the oral route). For example, for a compound(s) with low oral bioavailability, relatively higher doses may have to be administered. A daily dosage of the compound(s) (or combination in total) can be expected to be about 0.05 mg/kg bodyweight to about 1,000 mg/kg bodyweight, for example from about 0.1 mg/kg bodyweight to about 100 mg/kg bodyweight, for example from about 1 mg/kg bodyweight to about 50 mg/kg bodyweight. The daily dose may be administered as single dose or in divided doses and, in addition, the upper limit can also be exceeded when this is found to be clinically indicated.

Moreover, therapeutically effective amounts of the compound(s) may be co-administered with other agent(s), where the two agents are administered substantially simultaneously (e.g., as part of the same dosage form, or separately but at nearly same time~within less than an hour of each other) or in any sequential manner if clinically indicated.

Advantageously, administration of such therapeutically effective amounts of the compound(s) achieves inhibition of DYRK1A kinase activity in the subject or cell. Also of great importance is the ability or potential ability of the compound(s) to improve the symptoms of, slow the onset of, minimize, or even reverse, neurodegenerative diseases, such as AD, Down syndrome, Parkinson's disease, Huntington's disease, and the like through inhibition of DYRK1A kinase activity. The compound(s) can thus be useful for the treatment of AD and other amyloid-related disorders, or other conditions where inhibition of DYRK1A kinase activity is beneficial. For example, inhibition of DYRK1A kinase activity through therapeutic use of the compound(s) can be used to improve memory, learning, and/or counteracting age-related neurological disorders and diseases of the brain.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study, as well as for in vitro investigation in cell culture systems or other suitable assays where DYRK1A kinase activity and the effects of the compounds can be investigated.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

In order to determine the effectiveness of the DYRK1A inhibitors of the invention, a series of ELISA assays were performed, along with Western Blot assays.

The ELISA assays were devised as a modified form of the assay described in Liu et al. "An ELISA DYRK1A non-radioactive assay suitable for the characterization of inhibitors," F1000Research 2017, 6:42 (doi: 10.12688/f1000research.10582.1), incorporated by reference herein in its entirety.

Specifically, human DYRK1A (Addgene #38913) and HT-PRD (Addgene #87755) plasmids were obtained from Addgene and were expressed and purified using Ni affinity chromatography, as explained below. Proteins were quantified by the conventional Bradford method and stored at −80° C. until used.

HT-PRD was diluted in dilution buffer (25 mM Tris-HCl, pH 7.4 and 100 mM NaCl) to 4 ng/µL and used to coat a 96-well plate (BD Falcon #353072) with 100 µL per well at 4° C. overnight.

The wells were next washed with dilution buffer 3 times to remove unbound materials, and then the wells were blocked with 150 µL blocking buffer (2% BSA, 1×PBS, and 0.25% Tween 20) at room temperature for 60 minutes with shaking on a shaker.

After the 60-minute shaking period, the wells were washed thoroughly with dilution buffer 3 times to prepare for the phosphorylation in the next step.

Duplicate DYRK1A phosphorylation reactions were performed in the wells with 100 µL reaction mixtures each containing 25 mM HEPES, pH 7.4, 100 mM NaCl, 5 mM MgCl2, 100 µM ATP, 1% DMSO, and 200 ng/mL DYRK1A. Separate reaction mixtures included a no-inhibitor DMSO control, harmine inhibitor, and different concentrations of the inhibitors of the present invention. The plate was left on a temperature-controlled shaker for 30 minutes at 30° C.

The phosphorylation reactions were terminated after the 30-minute shaking, by the addition of 20 mM EDTA. The wells were then washed with PBST (0.02% Tween 20).

HT-PRD phosphorylation was determined by the sandwich antibody staining protocol. Specifically, 100 µL primary antibody (Dynamin 1a pS857-specific mouse mAb 3D3 from DSHB) (1.5 µg/mL) was added to each well and the plate was left on a shaker for 60 minutes at room temperature. Then the wells were washed with PBST, followed by the addition of AP-linked secondary antibody (Goat Anti-Mouse IgG Fab-AP, Southern Biotech, Cat #1015-04), with an incubation of 60 minutes at room temperature. The wells were then washed again with PBST. Finally, 100 µL PNPP solution was added to each well for calorimetric measurements. The extent of the phosphorylation reactions was monitored at $\lambda=405$ nm.

DYRK1A protein purification: In order to express DYRK1A protein, one-shot *E. coli* BL21(DE3) (Invitrogen) was transformed with DYRK1A-pNIC28 vector (Addgene, Cat #38913). The bacteria were grown at 37° C. in LB medium containing 50 µg/ml kanamycin until A600 nm reached about 0.7, followed by 1 mM IPTG induction of protein expression at 21° C. for 16 hours. The DYRK1A protein was then purified using the standard protocol for Ni-NTA purification.

HT-PRD protein purification: In order to express HT-PRD protein, one-shot *E. coli* BL21(DE3) (Invitrogen) was transformed with pHT-PRD pND1 vector (Addgene, Cat #87755). The bacteria were grown at 37° C. in LB medium containing 100 µg/ml ampicillin until A600 nm reached about 0.7, followed by 1 mM IPTG induction of protein expression at 21° C. for 16 hours. The pHT-PRD protein was purified using the standard protocol for Ni-NTA purification.

Western Blot Assays: Inducible WT tau HEK cells were treated for 24 hours with indicated fractions at final concentrations of 1 µg/mL. The cells were lysed and normalized by Bicinchoninic Acid (BCA) assay. Equal protein masses for each sample were loaded into acrylamide gels and separated by electrophoresis. Gel contents were transferred to PVDF membranes, blocked with a 7% non-fat dry milk solution, and probed with antibodies selective for total or phosphorylated (pTau) species. Band intensities were normalized to 8-actin (loading control) by densitometry. Changes were assessed as a % of DMSO (control) sample.

Solid particulate thymoquinone and harmaline at a 2:1 weight ratio were dissolved in an excess of ethanol, and allowed to react overnight at room temperature. After the reaction period, a number of test samples were recovered and used in the ELISA assay.

Specifically, a sample was first taken of the reaction mixture without any separations, which was labeled the crude all sample. The reaction mixture was then separated using HPLC into seven different fractions, based upon retention time. Fractions 2 and 4 of these initial seven fractions showed activity. Then, crude samples of fractions 2 and 4 were then recovered and named crude 2 and crude 4. Fraction 2 was then further separated into 15 fractions via HPLC, these being labeled fractions 2.1-2.15. Fraction 4 was further separated to obtain samples named fractions 4.1, 4.2, 4.3, and 4.4. Samples 4.1 and 4.2 were purified compounds I and II, respectively, as described above, and fractions 4.3 and 4.4 were mixed compound fractions.

The above-described fractions were then tested using the ELISA procedure, at the following concentrations. The results of these ELISA are set forth in the FIGURE, which lists fractions 1-25, defined below:

| Fraction # | Test samples |
|---|---|
| 1 | DMSO control; |
| 2-16 | fractions 2.1-2.15, each tested at 5 µg/mL; |
| 17 | fraction 4.1 (compound XVII), at 5 µg/mL; |
| 18 | fraction 4.2 (compound XVIII), at 5 µg/mL; |
| 19 | fraction 4.3, at 5 µg/mL; |
| 20 | fraction 4.4 at 5 µg/mL; |
| 21 | harmine 2 µM; |
| 22 | harmine 10 µM; |
| 23 | fraction crude 2, at 100 µg/mL; |
| 24 | fraction crude 4, at 100 µg/mL; |
| 25 | fraction crude all, at 100 µg/mL. |

FIG. 1 is a bar diagram depicting the effectiveness of DYRK1A inhibition using the above 25 test samples. As illustrated in the FIGURE, fractions 4.1 and 4.2 corresponding to compounds XVII and XVIII, exhibited very pronounced inhibition of DYRK1A, significantly greater than DSMO and any of the other fractions at the same level of use. In addition, although harmaline and the crude mixtures also demonstrated showed inhibition of DYRK1A, these compounds were tested at much higher concentrations (100 µg/mL) as compared to the concentration tested for compounds XVII and XVIII (5 µg/mL).

The invention claimed is:

1. One or more compounds having the structure I and/or II:

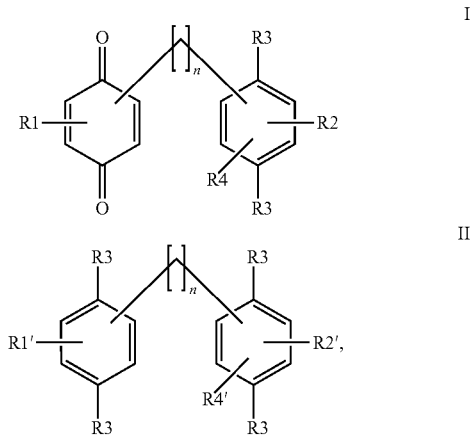

wherein:
  the linker -[ ]$_n$- is a branched or unbranched alkyl or alkenyl group, where n is from 1-6;
  each R1, R2, R4, R1', R2', and R4' are independently selected from the group consisting of —H, branched alkyl groups, and unbranched alkyl groups;
  each R3 is independently selected from the group consisting of hydroxyls, alkoxyls, straight and branched alkyl groups, halogenated derivates thereof, and halogens, provided that at least one of the six-membered rings in a pair comprises at least one oxygen-bearing substituent;
  optionally wherein one or more carbon atoms of the linker and/or any of R1, R2, R3, R4, R1', R2', and R4' may be independently substituted with a halogen or hydroxyl group, subject to the proviso that at least one of R2 and R4 in compound I is an isopropyl group, and/or at least one of R2' and R4' in compound II is an isopropyl group.

2. The one or more compounds of claim 1, wherein at least one of R2 or R4 in compound I is a methyl group, or wherein at least one R2' or R4' in compound II is a methyl group.

3. The one or more compounds of claim 1, where the linker -[ ]$_n$- is a methylene bridge.

4. The one or more compounds of claim 1, at least one of R2 or R1 in compound I is an isopropyl group, or wherein at least one R1' or R2' in compound II is an isopropyl group.

5. The one or more compounds of claim 1, wherein the structures are selected from the group consisting of:

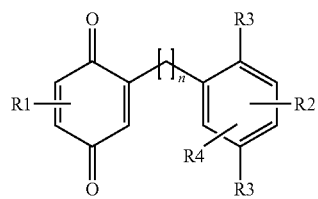
III

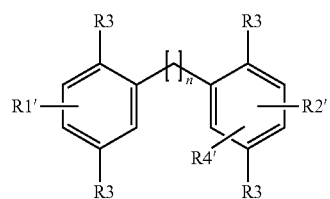
IV

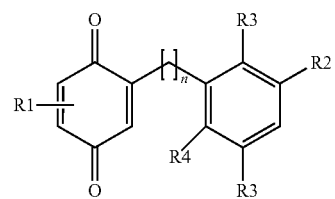
V

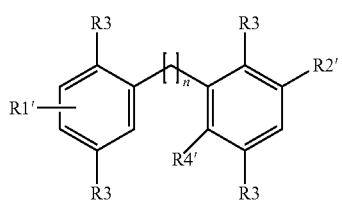
VI

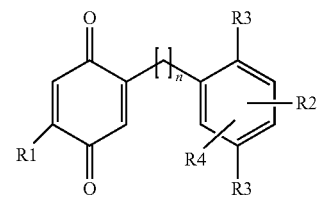
VII

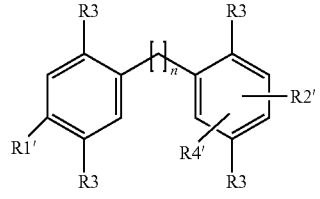
VIII

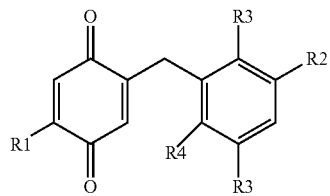
IX

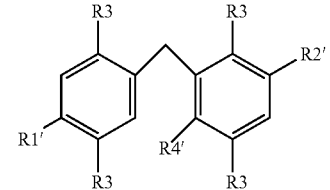
X wherein n, R1, R2, R3, R4, R1', R2', and R4' are as defined in claim 1.

6. The one or more compounds of claim 1, wherein the structures are

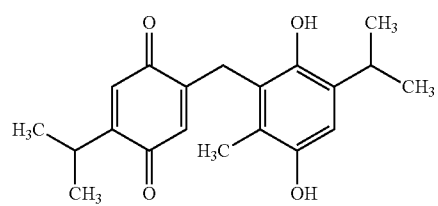
XVII and/or

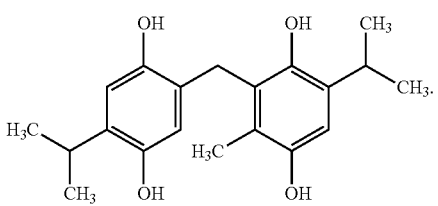
XVIII

7. The one or more compounds of claim 1, said compounds selected from the group consisting of the isomers, tautomers, esters, metal complexes, and salts of the structures.

8. A composition comprising a plurality of one or more compounds of claim 1 dispersed in a carrier.

9. The composition of claim 8, comprising a plurality of compounds according to structure I and a plurality of compounds according to structure II dispersed in said carrier.

10. A method of inhibiting DYRK1A activity comprising the step of contacting DYRK1A kinase with an effective amount of a thymoquinone derivative comprising a pair of substituted or unsubstituted six-membered carbon rings selected from the group consisting of phenyl and cyclohexadiene linked by a linker bonded to both of said six-membered rings, at least one of said six-membered rings having a pair of oxygen-bearing substituents selected from the group consisting of carbonyl oxygens, hydroxyls, alkoxyls, and halogenated derivatives thereof, said linker being a straight or branched chain alkyl or alkenyl group having from 1-6 carbon atoms.

11. The method of claim 10, wherein said thymoquinone derivative is a compound having the structure I and/or II:

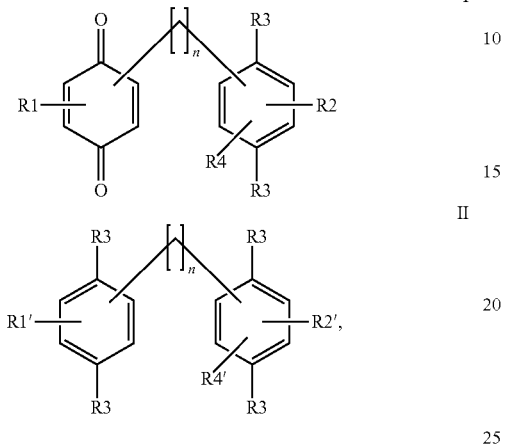

wherein:
- the linker -[ ]$_n$- is a branched or unbranched alkyl or alkenyl group, where n is from 1-6;
- each R1, R2, R4, R1', R2', and R4' are independently selected from the group consisting of —H, branched alkyl groups, and unbranched alkyl groups;
- each R3 is independently selected from the group consisting of hydroxyls, alkoxyls, straight and branched alkyl groups, halogenated derivates thereof, and halogens, provided that at least one of the six-membered rings in a pair comprises at least one oxygen-bearing substituent;
- optionally wherein one or more carbon atoms of the linker and/or any of R1, R2, R3, R4, R1', R2', and R4' may be independently substituted with a halogen or hydroxyl group, subject to the proviso that at least one of R2 and R4 in compound I is an isopropyl group, and/or at least one of R2' and R4' in compound II is an isopropyl group.

12. The method of claim 10, wherein both of said six-membered rings are phenyl and each of said oxygen-bearing substituents is OH, or a halogenated derivative thereof.

13. The method of claim 10, wherein one of said six-membered rings is phenyl and the other six-membered ring is cyclohexadiene, the oxygen-bearing substituents of said phenyl are both OH, or a halogenated derivative thereof, and the oxygen-bearing substituents of said cyclohexadiene are both O.

14. The method of claim 10, wherein each of said six-membered rings includes an alkyl substituent having from 1-6 carbon atoms.

15. The method of claim 14, wherein one of the alkyl substituents on each ring is an isopropyl group.

16. The method of claim 10, said linker being a CH2 methylene bridge.

17. The method of claim 10, wherein said thymoquinone derivative is a compound having a structure selected from the group consisting of:

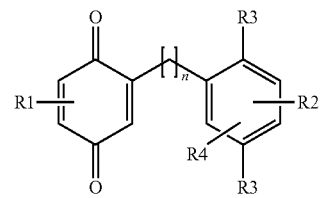

III

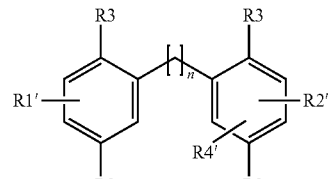

IV

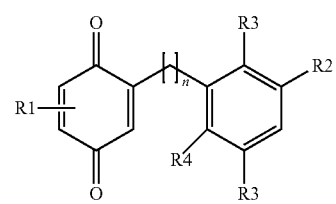

V

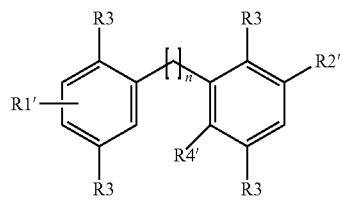

VI

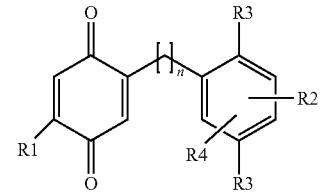

VII

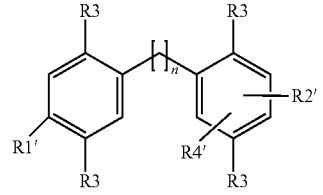

VIII

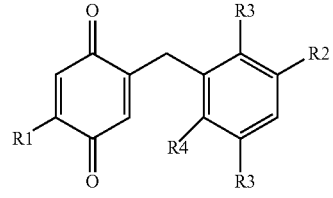

IX

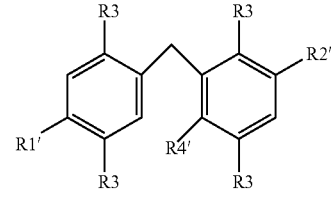

X wherein the linker -[ ]$_n$-, when present, is a branched or unbranched alkyl or alkenyl group, where n is from 1-6;

each R1, R2, R4, R1', R2', and R4' are independently selected from the group consisting of —H, branched alkyl groups, and unbranched alkyl groups;

each R3 is independently selected from the group consisting of hydroxyls, alkoxyls, straight and branched alkyl groups, halogenated derivates thereof, and halogens, provided that at least one of the six-membered rings in a pair comprises at least one oxygen-bearing substituent;

optionally wherein one or more carbon atoms of the linker and/or any of R1, R2, R3, R4, R1', R2', and R4' may be independently substituted with a halogen or hydroxyl group, subject to the proviso that at least one of R2 and R4 in compound III, V, VII, or IX is an isopropyl group, and/or at least one of R2' and R4' in compound IV, VI, VIII, or X is an isopropyl group.

18. The method of claim 10, wherein said thymoquinone derivative is

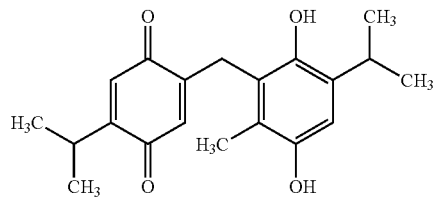

XVII and/or

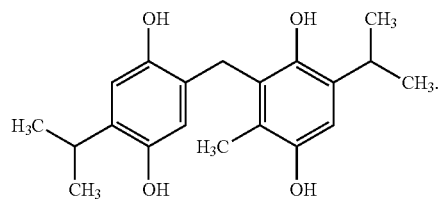

XVIII

19. The method of claim 10, wherein said effective amount of a thymoquinone derivative comprises a composition comprising a plurality of thymoquinone derivatives dispersed in a carrier.

20. The method of claim 10, wherein said contacting step comprises administering an effective amount of said thymoquinone derivative to a subject in need thereof.

21. The one or more compounds of claim 1, wherein each R3 is a straight or branched C1-C6 alkyl group.

* * * * *